(12) United States Patent
Walsh

(10) Patent No.: US 7,074,362 B2
(45) Date of Patent: Jul. 11, 2006

(54) METHOD OF PREPARING AND STERILIZING AN INSTRUMENT CONTAINING PACKAGE AND APPARATUS

(76) Inventor: James L. Walsh, P.O. Box 123, Perth, ON (CA) K7H 3E3

( * ) Notice: Subject to any disclaimer, the term of this patent is extended or adjusted under 35 U.S.C. 154(b) by 826 days.

(21) Appl. No.: 10/106,789

(22) Filed: Mar. 26, 2002

(65) Prior Publication Data
US 2003/0185703 A1  Oct. 2, 2003

(51) Int. Cl.
A61L 2/08 (2006.01)

(52) U.S. Cl. .............. 422/1; 53/477; 53/478; 53/552; 53/289; 206/439; 422/26

(58) Field of Classification Search .......... 422/1, 422/26; 383/113; 206/439; 53/441, 176, 53/512, 455, 477, 478, 548, 552, 289, 290
See application file for complete search history.

(56) References Cited

U.S. PATENT DOCUMENTS

| 3,552,638 | A | * | 1/1971 | Quackenbush | 206/484 |
|---|---|---|---|---|---|
| 3,597,587 | A | | 8/1971 | Baum | |
| 3,731,054 | A | | 5/1973 | Bair | |
| 3,901,759 | A | | 8/1975 | Highfield et al. | |
| 3,909,334 | A | | 9/1975 | Verbeke | |
| 4,062,718 | A | | 12/1977 | Hay, II | |
| 4,407,874 | A | * | 10/1983 | Gehrke | 428/35.2 |
| 4,433,527 | A | | 2/1984 | Ramsey et al. | |
| 4,568,818 | A | | 2/1986 | Ikemoto | |
| 4,767,482 | A | | 8/1988 | Diez et al. | |
| 4,792,373 | A | | 12/1988 | Hsei et al. | |
| 4,941,310 | A | | 7/1990 | Kristen | |
| 5,253,754 | A | | 10/1993 | Soodak | |
| 5,335,483 | A | * | 8/1994 | Gavronsky et al. | 53/451 |
| 5,458,730 | A | | 10/1995 | Soodak | |
| 5,474,637 | A | | 12/1995 | Soodak | |
| 5,730,530 | A | | 3/1998 | Stoddard et al. | |
| 5,851,069 | A | | 12/1998 | Davoren | |
| 6,119,439 | A | * | 9/2000 | Stevie | 53/455 |
| 6,119,590 | A | | 9/2000 | Hutchinson | |
| 6,186,933 | B1 | | 2/2001 | DeMatteis | |
| 6,256,968 | B1 | * | 7/2001 | Kristen | 53/512 |
| 6,294,210 | B1 | * | 9/2001 | Kuo | 426/127 |
| 6,490,844 | B1 | * | 12/2002 | Jones | 53/441 |

* cited by examiner

*Primary Examiner*—Krisanne Jastrzab
(74) *Attorney, Agent, or Firm*—Roger Aceto, Esq.; Stephen B. Salai, Esq.; Harter, Secrest & Emery LLP

(57) ABSTRACT

A method for preparing dental instruments for sterilization in which the instruments are put into a relatively large see-through heat sealable plastic bag. The bag is placed over a surface of an impulse heater and an arm is lowered to clamp the bag and apply two heat seals across the bag; one heat seal to enclose the instruments and a second parallel heat seal. A knife carried by the arm is used to cut between the two heat seals. This cutting operation forms a custom sized closed bag containing the instruments to be sterilized that is placed into an autoclave and sterilized. The cutting also forms a second bag, smaller than the original bag that is reserved for use in a subsequent packaging operation.

13 Claims, 3 Drawing Sheets

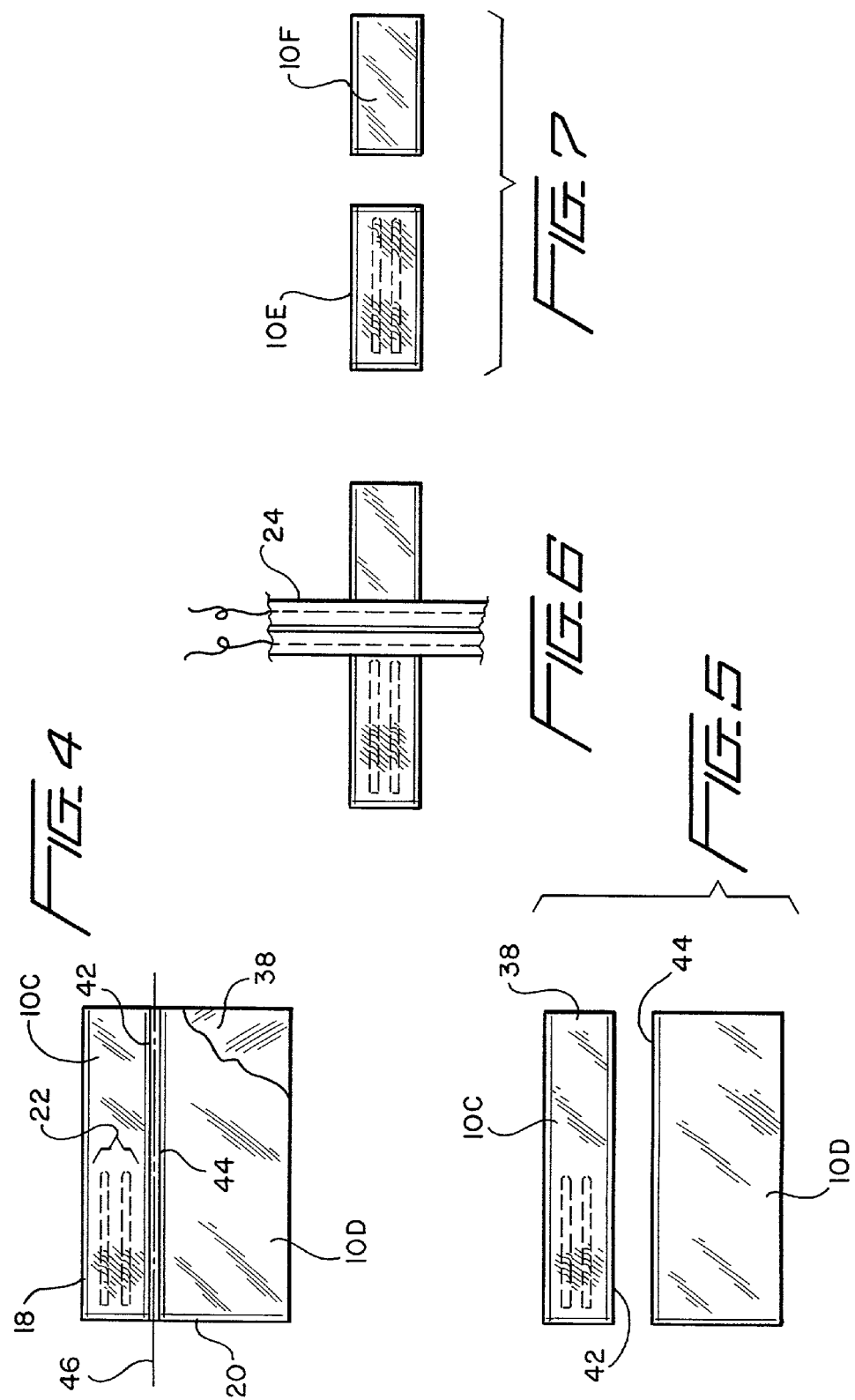

METHOD OF PREPARING AND STERILIZING AN INSTRUMENT CONTAINING PACKAGE AND APPARATUS

TECHNICAL FIELD

The present invention relates to a sterilizing method and more particularly to preparing a package for steam sterilizing and to apparatus for preparing the package.

BACKGROUND OF THE INVENTION

The offices of medical and dental practitioners usually contain one or more autoclaves or steam sterilizers for sterilizing reusable medical and dental instruments. For example, in a dental office the autoclave is used to sterilize picks, mirrors, drill bits, hand pieces and the like. At one time the instruments to be sterilized were put on a tray and then placed into the sterilizer. While this sterilized the instruments, the aseptic conditions were not necessarily maintained if the instruments were mishandled in removing them from the sterilizer.

Autoclave pouches then were introduced for holding the instruments during sterilizing. The pouches generally comprise a strip of plastic film sealed on three sides to a paper backing. Instruments to be sterilized are loaded into the pouch, the pouch is sealed and then it is placed into the autoclave. Usually the pouch includes an indicator that changes color to indicate that the contents have reached a sterilizing temperature. Generally this is 135–137° C. After sterilization, the instruments are kept in the pouch until they are needed. Thus the pouches provide a barrier to recontamination and can be handled and moved without the risk of contaminating the sterilized instruments within the pouch. Since the instruments can be of various sizes, it is necessary for the dental/medical or other health practitioner to keep a supply of pouches in various sizes on hand.

In a more recent advancement, the instruments are put into a see-through plastic bag. The bag is heat sealed and then put into the autoclave. Plastic bags are a more viable alternative to the paper/plastic pouches in several respects. For example, plastic bags are less expensive to manufacture than the paper/plastic pouches and are easier to recycle. Plastic bags also are more convenient in that the contents can be viewed through either side of the bag rather than just the clear side of the paper/plastic pouch. Also there is no need to stock a variety of sizes. Fewer sizes can be stocked because the bags can be heat sealed so a practitioner can subdivide a larger bag into smaller custom sized units. This is done prior to use by cutting a larger bag either transversely or longitudinally and then applying additional heat seals to form a smaller bag. Cutting and forming smaller bags either can be done in advance of loading instruments into a bag or after loading. For example, a small instrument can be loaded into a larger bag. The bag then is closed by heat sealing close to the instrument and then the excess material is cut off. The excess material, which now is open at its opposite ends, is heat sealed across one end to form a new bag that is smaller in one dimension than the original bag.

While the use of plastic bags in this manner has found some acceptance, the procedure required the repeated operation of the heat sealer to close a first bag and then to form a second bag. The present invention addresses this problem and simplifies the sterilizing procedure by reducing the steps of closing and forming bags.

SUMMARY OF THE INVENTION

In accordance with the present invention, the operation of preparing articles for sterilization is simplified. In this respect the articles to be sterilized are loaded into a plastic bag, the bag is heat sealed and then placed into the sterilizer as is conventional. However, in the present invention a few articles or smaller articles can be placed into a larger bag and the bag size is reduced to a custom size that closely fits its contents. This conserves both space in the sterilizer and bag material. Reduction of the bag size is accomplished by simultaneously applying a first transverse heat seal to close the bag and a second parallel heat seal. A cut is made between the heat seals to separate the closed bag from the excess material. The excess material having a heat seal at one end then forms a second bag that is shorter than the original and is ready to receive other articles to be sterilized.

Accordingly, the present invention may be characterized in one aspect thereof by a method for sterilizing dental and medical instruments comprising:

a) providing an original plastic bag that is larger than is needed to contain an instrument to be sterilized, the bag having a closed end and an opposite open end and the bag being composed of a plastic material that is heat sealable and able to withstand moist heat sterilizing conditions;
b) inserting an article to be sterilized into the plastic bag;
c) applying a first transverse heat seal to close the bag at a location adjacent the article and simultaneously applying a second transverse heat seal spaced from and parallel to the first heat seal;
d) cutting between the heat seals to form a closed, article-containing custom sized bag and a second bag having an open end;
e) placing the article-containing custom sized bag into an autoclave; and
f) holding the article-containing custom sized bag in the autoclave under conditions sufficient to sterilize the article.

In another aspect the present invention may be characterized by a heat sealer for preparing a sterilizable instrument-containing bag comprising:

a) an elongated housing having a platen that accommodates a portion of a heat sealable plastic bag draped across the platen, the bag containing an article to be sterilized;
b) an arm movable against the platen to capture the heat sealable bag between the arm and the platen;
c) parallel heat sealing elements activated upon the movement of the arm against the platen to provide the plastic bag with two heat seals, a first of the heat seals closing the bag to seal its contents therein and a second of the heat seals being parallel to the first heat seal; and
d) a knife carried by the arm and movable along the arm, the knife being operable prior to the removal of the arm from against the platen to cut between the heat seals thereby forming a first closed instrument-containing custom sized bag for sterilizing and a closed bottom of a second bag for subsequent use.

DESCRIPTION OF THE DRAWINGS

FIGS. 1–3 are schematic views showing the sequence of steps in the method of the present invention;

FIGS. 4–7 are schematic views showing another embodiment of the invention;

Figure 1:
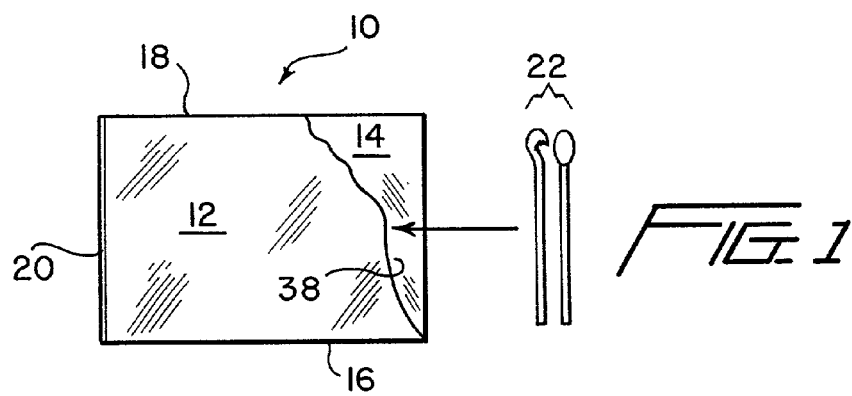
Figure 8:
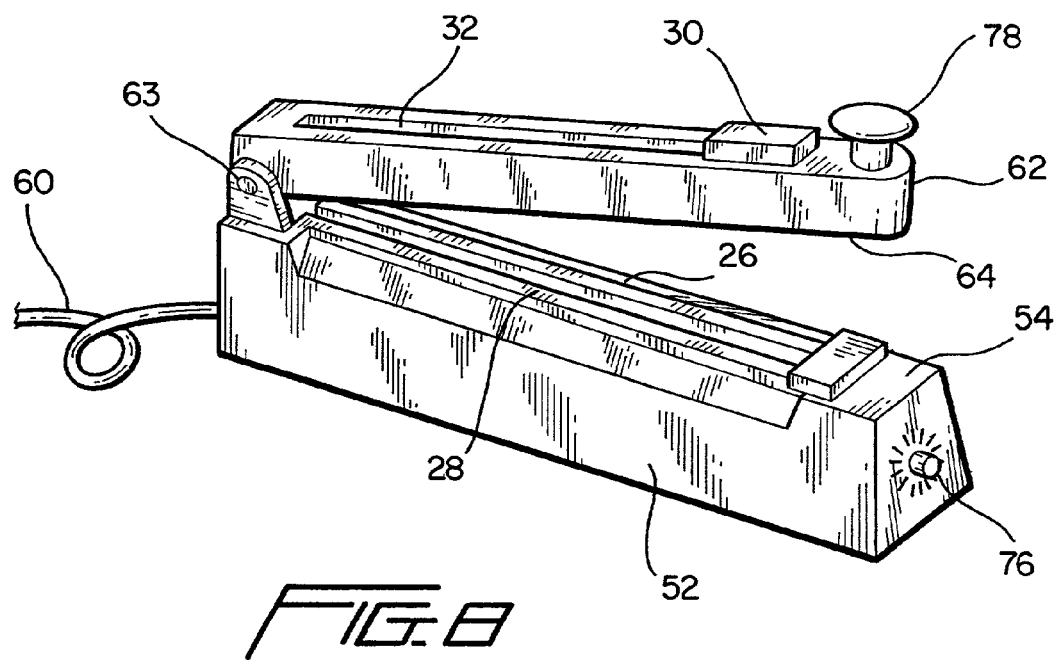
Figure 9:
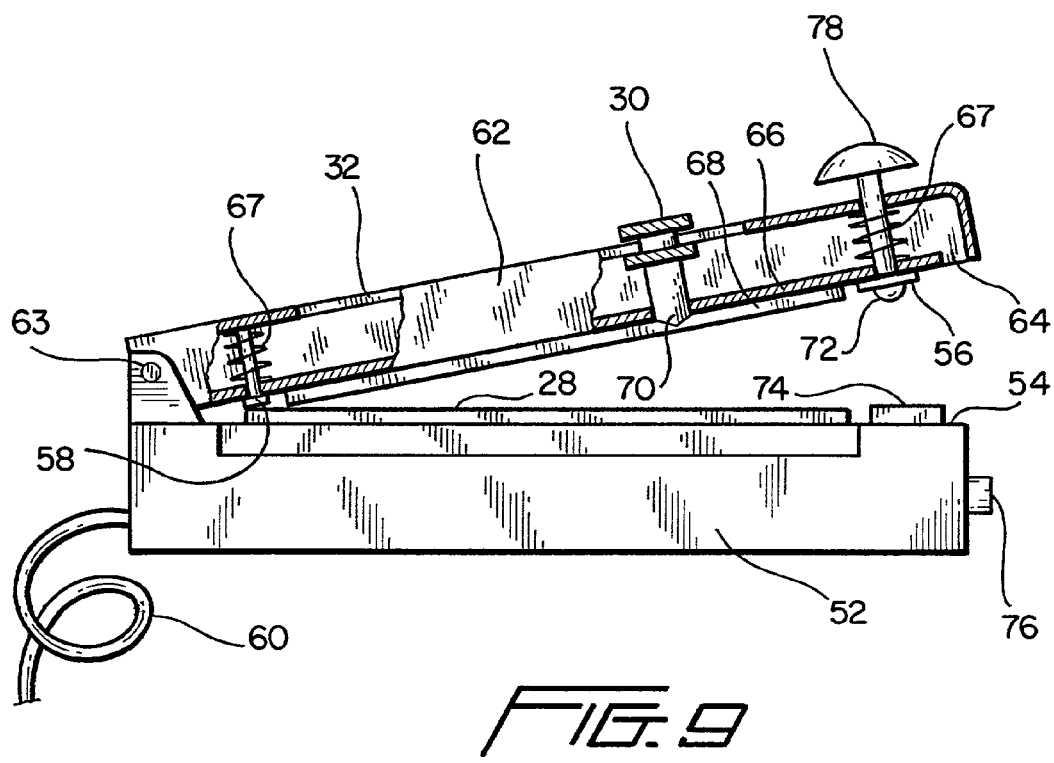

FIG. 8 is a perspective view of the heat sealer according to the present invention; and FIG. 9 is a side elevation view of the heat sealer of FIG. 1 on an enlarged scale and partly broken away.

DETAILED DESCRIPTION OF THE INVENTION

Figure 2:
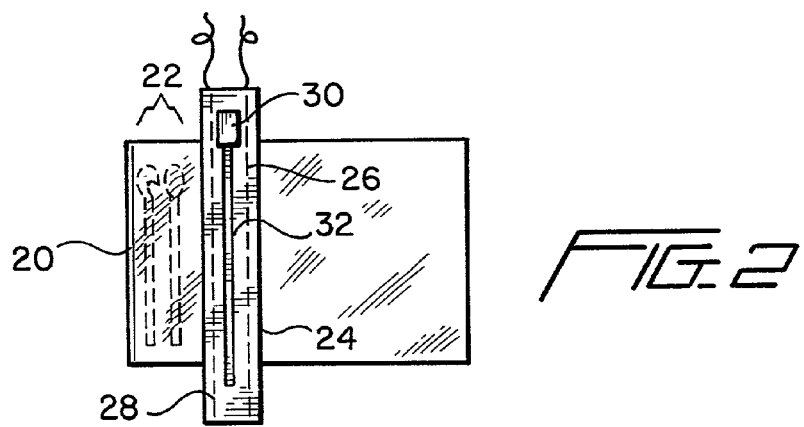
Figure 3:
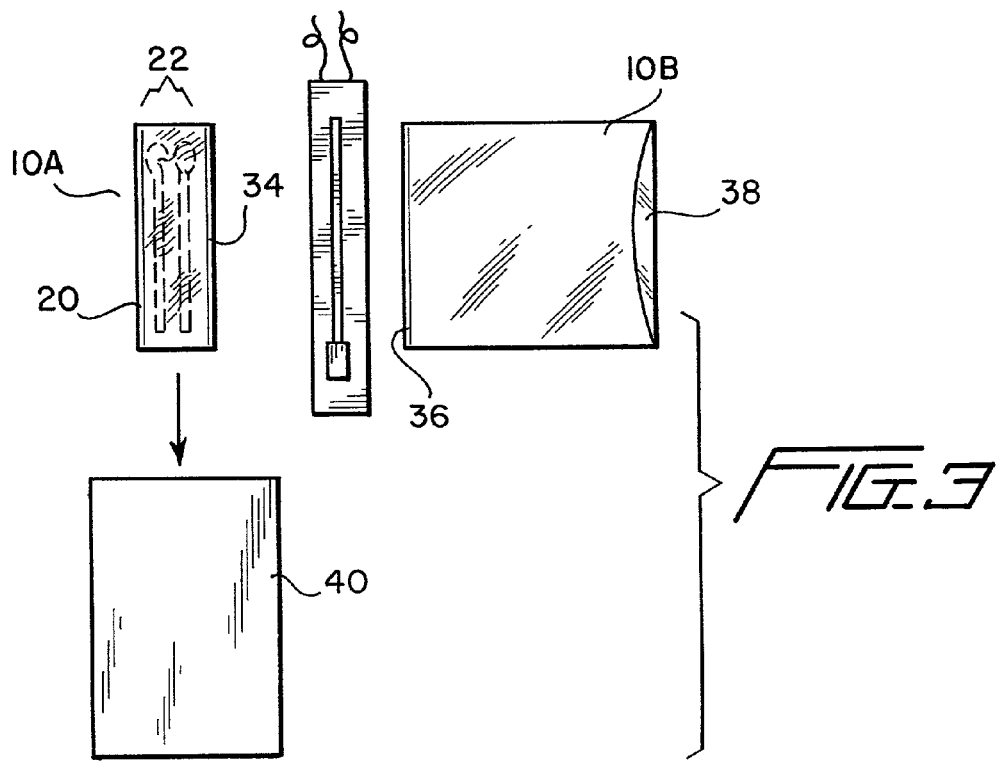

Referring to the drawings, FIGS. 1–3 show the sequence of steps in performing the method of the present invention. In this respect FIG. 1 shows a clear plastic bag 10 of the type that is conventionally used by a dental, medical or other health practitioner to sterilize instruments. The bag, also referred to as a pouch, is made of a conventional plastic such as a 2 mil polyethylene or any other plastic that is heat sealable and is sufficiently temperature resistant to withstand the moist heat conditions of time, temperature and moisture in a steam sterilizer or autoclave. For example, the temperature within an autoclave must reach 135° C. to 137° C. for extended periods in order to insure sterilization of articles within the sterilizer.

While there are various bag configurations, a stock bag or pouch used in steam sterilization is formed of a flattened tubular film. In this respect flattening the tubular film forms the front and rear panels 12, 14 respectively of the bag and the bag side edges 16, 18 are fold lines of the flattened tube. A transverse heat seal that seals the front and rear panels together forms the bottom 20 of the bag.

As a first step in the method, one or more articles to be sterilized such as a dental pick and mirror indicated at 22 are inserted into the open end 38 of an original bag 10 and are moved to the closed bottom of the bag. The bag is then delivered to a heat sealer 24 (FIG. 2). A portion of the bag is positioned so the heat sealer extends across the bag and is as close as possible to the articles 22 at the bottom of the bag.

As further described hereinbelow, the heart sealer has two parallel heating elements 26, 28 that are heated to heat seal the bag. Preferably the heating elements are components of an impulse heater. Disposed between the two heating elements is a knife 30 that is movable along a slot 32 from one end of the heat sealer to the other. After placement in the heat sealer, the heating elements 26, 28 are energized for a time sufficient to form two closely spaced heat seals extending across the bag. The knife 30 then is operated to cut between the heat seals. The result is shown in FIG. 3.

As shown in FIG. 3, the heat sealing and cutting operations form a closed custom-sized bag 10A containing the articles 22 to be sterilized and a second bag 10B that is shorter than the original bag 10 of FIG. 1. The closed bag 10A includes the original bottom 20 of the original bag and is closed by a heat seal 34 formed by the heating element 28. The second bag 10B has a closed bottom 36 formed by the heating element 26 and the open end 38 of the original bag 10.

The closed custom-sized bag 10A containing the instruments now is delivered to a sterilizer 40 while the second bag 10B is set aside for further use as an "original bag" in a subsequent packaging/sterilizing operation. In this respect the second bag 10B is shorter than the original but still can be used in one or more additional packaging operations as described above. As long as a second bag 10B resulting from a packaging operation is large enough, a single original bag can be customized several times. Each packaging operation produces a sealed bag together with a second shorter bag that is available for use as an "original bag" and ready to receive articles to be sterilized. Since the sealing operation applies a double seal, the closing of one bag and the preparation of another is facilitated.

While FIGS. 1–3 show an arrangement where the seals 34, 36 applied to the bag 10 are transverse seals, it should be appreciated that instruments also can be inserted longitudinally into the bag. Such an arrangement is shown in FIGS. 4–7. In FIG. 4, the instruments 22 are inserted lengthwise and are positioned close to a side edge 18 of the original bag 10 bag. The original bag 10 then is placed into the heat sealer (not shown) cross wise so the heating elements form two longitudinally extending seals 42, 44. These heat seals are normal to the closed bottom 20 and extend from the closed bottom 20 to the open end 38. The bag then is cut between the seals along the line 46 to separate the instrument-containing bag 10C from a second bag 10D (FIG. 5). Both the bags 10C and 10D now are considered side-sealed bags in that the heat seals 42, 44 form a closed side of each of the bags 10C and 10D respectively. The bag 10D is reserved for a subsequent packaging operation whereas bag 10C must undergo further operations prior to placing it into a sterilizer.

As shown in FIG. 5, the instrument-containing bag 10C is still open at its end 38 and must be sealed prior to loading into a sterilizer. This is done by placing the bag into the heat sealer 24 (FIG. 6), making two transverse heat seals and then cutting between the heat seals as described hereinabove with respect to FIG. 2. The result as shown in FIG. 7 is a closed custom sized side-sealed bag 10E ready for the sterilizer and a smaller open side sealed bag 1OF that can be reserved for another packaging operation, size permitting.

Heat sealer 24 is further described with reference to FIGS. 8 and 9. FIG. 8 shows the heat sealer as comprising an elongated base or housing portion 52 having a flat upper surface 54. The upper surface 54 defines a platen over which a portion of a plastic bag is laid or draped for heat sealing. Laid along the platen are the two heating elements 26, 28. Each heating element itself is conventional and need not be described in detail. It is sufficient to say that each heating element includes a resistance wire covered with a non-stick fabric. The heating elements are part of an electric circuit including components (not shown) disposed within the housing that together comprise an impulse heater that also is conventional. When energized, the impulse heater heats the heating elements 26, 28 for a time sufficient to complete a heat sealing operation.

A pivot connection 63 attaches one end of arm 62 to an end of the elongated base or housing portion 52. The housing has a hollow interior and is open at its bottom 64. Disposed within the arm as shown in FIG. 9, is a plate 66. The plate is spring-loaded and is biased by springs 67 for movement out through the arm open bottom 64. Stops 56, 58 serve to retain the plate to the arm. Carried by the plate are two resilient backing member 68, one of the backing members being associated with each of the heating elements 26, 28. During operation of the heat sealer the backing members press against the heating elements as described hereinbelow.

The arm also has the slot 32 that slidably receives the knife 30. The tip 70 of the knife extends between the backing members 68. With the backing members in the position as shown in FIG. 9, the knife tip is not exposed and does not extend below the level of the backing members.

Completing the structure is a contact 72 on the arm and a corresponding contact 74 on the housing. The contacts are part of the impulse heating circuit and when closed cause the energizing of the heating elements.

In operation, the heat sealer has its electrical cable 60 connected to a power source. A dial 76 then is adjusted to set the duration of the impulse heating cycle. With the arm 62 in a raised position as shown in FIGS. 8 and 9, a bag 10 (FIGS. 1–3) to be sealed is laid across the upper surface 54 of the housing so that an unfilled portion of the bag is draped over the heating members 26, 28. Lowering the arm brings the backing members 68 towards the heating members 26, 28. Since the plate 66 and backing members 68 are spring loaded, closing them against the heating elements moves the plate and backing members against the spring bias and into the hollow interior of the arm. In this way a bag, laid across to upper surface 54 of the housing is held in position and is clamped between the heat seal elements 26, 28 and the backing members 68.

The arm is pivoted to a closed position by pressing on the knob. In a closed position, the contact 72 on the arm and the contact 74 on the housing touch. This closes a circuit to energize the heating elements 26, 28 and effect the impulse heating of the heating elements to form heat-seals 34, 36 across the bag. After an appropriate period, the impulse heater circuit times out and the circuit is interrupted to de-energize the heating elements.

It should be appreciated that as the backing members 68 move into the hollow interior of the arm 62, the knifepoint 70 is exposed. Accordingly, with the arm held in the closed position, the knife 30 can be drawn along the slot 32 to cut between the parallel heat seals to separate the closed custom sized bag 10A from the newly formed bag 10B. It should be understood that even though the arm 62 is held in the closed position and the contacts 72, 74 remain in contact the heating elements remain de-energized until the contact between contacts 72, 74 is broken. After the contact is broken, by raising the arm to the position shown in FIGS. 8 and 9 the heating elements can be energized by again closing the contacts.

Thus it should be appreciated that the present invention provides a method of preparing a sterilizable package including steps for preparing a package for sterilization that simplifies the preparation and the sterilization process. The method allows enclosing a few articles into a larger bag and then sealing the bag for placement into a sterilizer in a manner that custom sizes the bag by removing any excess portion while simultaneously preparing the excess portion to receive other articles for sterilizing. Removing the excess bag material provides a neater package for the fewer articles and conserves space in the sterilizer. This also is less wasteful of the bag material. As the removed portion can be used in subsequent packaging operations. Closing the bag and simultaneously applying a bottom seal for another bag facilitates the operation by eliminating the step of forming the bottom seal of the second bag in a separate operation.

What is claimed is:

1. A method for sterilizing dental and medical instruments comprising:
    a) providing an original plastic bag that is larger than is needed to contain an instrument to be sterilized, the bag having a closed end and an opposite open end and the bag being composed of a plastic material that is heat sealable and able to withstand moist heat sterilizing conditions;
    b) inserting an article to be sterilized into the plastic bag;
    c) applying a first transverse heat seal to close the bag at a location adjacent the article and simultaneously applying a second transverse heat seal spaced from and parallel to the first heat seal;
    d) cutting between the heat seals to form a closed, article-containing custom sized bag and a second smaller bag having an open end;
    e) placing the articl-econtaining custom sized bag into an autoclave;
    f) holding the article-containing custom sized bag in the autoclave under conditions sufficient to sterilize the article; and
    g) reserving the second smaller bag and repeating steps b–f in sequence at least one additional time using the second smaller bag as the original bag to form a second closed article-containing custom sized bag and a third smaller bag.

2. A method as in claim 1 wherein the article to be sterilized comprises a dental instrument.

3. A method as in claim 1 wherein the inserting step comprises locating the article in a transverse position in the original bag and adjacent the closed end.

4. A method as in claim 1 wherein the inserting step comprises locating the article to be sterilized in the original bag along a side edge of the original bag and then, prior to the step of applying the first and second transverse seals, performing the steps of:
    a) applying a first longitudinal heat seal extending from the closed end of the original bag to the open end along side and adjacent the article and simultaneously applying a second longitudinal heat seal parallel to the first longitudinal heat seal;
    b) cutting between the two longitudinal heat seals to form a first open ended side sealed bag containing the article and a second open ended side sealed bag; and thereafter
    c) taking the first open ended side sealed bag and performing the claim 1 steps of applying the first transverse heat seal to close the bag at a location adjacent the article, simultaneously applying the second transverse heat seal spaced from and parallel to the first heat seal, cutting between the heat seals to form the closed, article-containing custom sized bag and the second smaller bag having an open end, placing the articl-econtaining custom sized bag into an autoclave and holding the article-containing custom sized bag in the autoclave under conditions sufficient to sterilize the article.

5. A method as in claim 4 comprising reserving the second side sealed bag for a subsequent packaging and sterilizing operation wherein the second side sealed bag is used as an original bag.

6. A method for preparing and sterilizing an instrument containing bag comprising:
    a) providing an impulse heat sealer including
        i) a platen,
        ii) two parallel heat sealing wires on the platen,
        iii) an arm movable from an open position to a closed position, the arm in the closed position pressing against the heat sealing wires, and
        iv) and a knife carried by and movable along the arm and between the heat sealing wires;
    b) locating an original heat sealable plastic bag containing an article be sterilized across the platen, the bag being larger than needed to accommodate the article and the bag having a closed end and an opposite open end and the bag being composed of a plastic material that is heat sealable and able to withstand moist heat sterilizing conditions;
    c) closing the arm to press the heat sealing wires against the bag and heating the wires thereby applying a first transverse heat seal to close the bag at a location adjacent the article and simultaneously applying a second transverse heat seal spaced from and parallel to the first heat seal;

d) maintaining the arm in the closed position while drawing the knife along the arm thereby cutting between the heat seals and forming a closed, article-containing custom sized bag and a second smaller bag having an open end;

e) placing the article-containing custom sized bag into an autoclave;

f) holding the article-containing custom sized bag in the autoclave under conditions sufficient to sterilize the article; and g) reserving the second smaller bag for later use in a subsequent method for preparing and sterilizing an article-containing bag wherein the second smaller bag is used as the original bag.

7. A heat sealer for preparing sterilizable instrument containing bags comprising:

a) an elongated housing having a platen that accommodates a portion of a heat sealable plastic bag draped across the platen, the bag containing an article to be sterilized;

b) an arm movable against the platen to capture the heat sealable bag between the arm and the platen;

c) parallel heat sealing elements activated upon the movement of the arm against the platen to provide the plastic bag with two heat seals, a first of the heal seals closing the bag to seal its contents therein and a second of the heat seals being parallel to the first heat seal; and d) a knife carried by the arm and movable along the arm, the knife being operable prior to the removal of the arm from against the platen to cut between the heat seals thereby forming a first closed instrument-containing custom sized bag for sterilizing and a closed bottom of a second bag for subsequent use.

8. Apparatus as in claim 7 wherein the arm has one end pivotally attached to the housing and a free end.

9. Apparatus as in claim 8 wherein the free end of the arm carries a contact member engageable against a corresponding contact member on the housing for energizing the heat sealing elements.

10. Apparatus as in claim 7 wherein the heat sealing elements are disposed on the platen.

11. Apparatus as in claim 10 wherein the arm has an open bottom and resilient backing members extend through the open bottom to press against the heat sealing elements upon movement of the arm against the platen.

12. Apparatus as in claim 11 wherein the backing members are spring biased and pressing the backing members against the heat sealing elements urges the backing members against the spring bias.

13. Apparatus as in claim 7 wherein the arm has a slot extending substantially the length of the arm and the knife extends through the slot and is slidable along the slot.

* * * * *

UNITED STATES PATENT AND TRADEMARK OFFICE
CERTIFICATE OF CORRECTION

PATENT NO. : 7,074,362 B2  Page 1 of 1
APPLICATION NO. : 10/106789
DATED : July 11, 2006
INVENTOR(S) : James L. Walsh It is certified that error appears in the above-identified patent and that said Letters Patent is hereby corrected as shown below:

Column 6, line 1
Replace "articl-econtaining"
With -- article-containing --

Column 6, line 36-37
Replace "articl-econtaining"
With -- article-containing --

Column 7, line 25
Replace "heal"
With -- heat --

Signed and Sealed this

Thirtieth Day of January, 2007

JON W. DUDAS
*Director of the United States Patent and Trademark Office*